United States Patent [19]

Leonard

[11] 4,219,618
[45] Aug. 26, 1980

[54] DENTAL HAND TOOL HOLDER

[75] Inventor: Henri Leonard, Besancon, France

[73] Assignee: Micro-Mega S.A., Besancon, France

[21] Appl. No.: 867,100

[22] Filed: Jan. 5, 1978

[30] Foreign Application Priority Data

Jan. 28, 1977 [FR] France .............................. 77 02946
Mar. 18, 1977 [FR] France .............................. 77 08749

[51] Int. Cl.² ........................................... A61G 17/02
[52] U.S. Cl. .................................................. 433/80
[58] Field of Search ...................... 251/341, 345, 352; 173/57; 32/28, 27; 433/80

[56] References Cited

U.S. PATENT DOCUMENTS 3,277,922 10/1966 Eisel ..................................... 251/34.5
4,107,846 8/1978 Fleer ......................................... 32/27

FOREIGN PATENT DOCUMENTS 2542826 3/1977 Fed. Rep. of Germany .............. 32/28

Primary Examiner—Robert Peshock
Attorney, Agent, or Firm—Robert E. Burns; Emmanuel J. Lobato; Bruce L. Adams

[57] ABSTRACT

A dental handpiece having a head adapted to receive the tool rotatably driven through a central shaft and having a rear end adapted to be coupled to a driving member adapted to rotate freely therein, comprises an internal inlet port for supplying cooling fluid to the tool which communicates with an outlet passage leading to the head of the holder. An external inlet port also communicating with the outlet passage via a chamber is provided; the internal inlet port opens into this chamber and a valve member adapted to close either of these ports is provided for permitting the communication between the open port and the outlet passage. This handpiece is adapted to be coupled to driving members provided or not with an internal passage for delivering cooling fluid to the tool.

16 Claims, 23 Drawing Figures

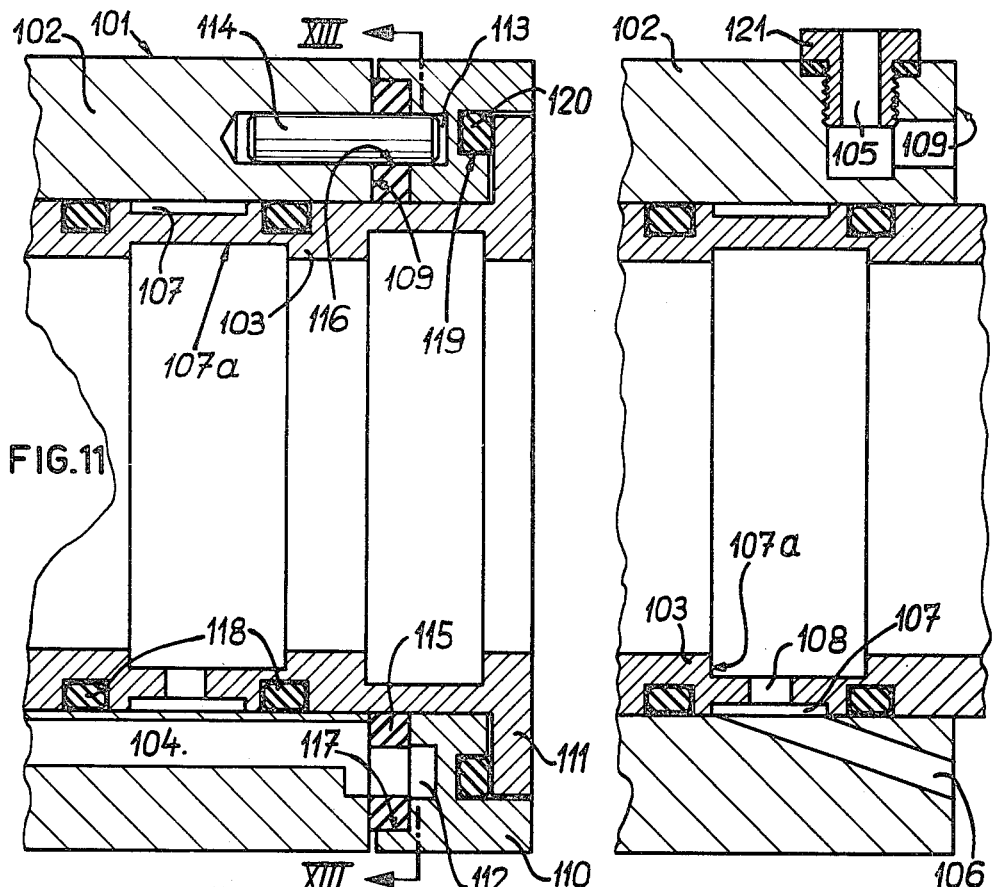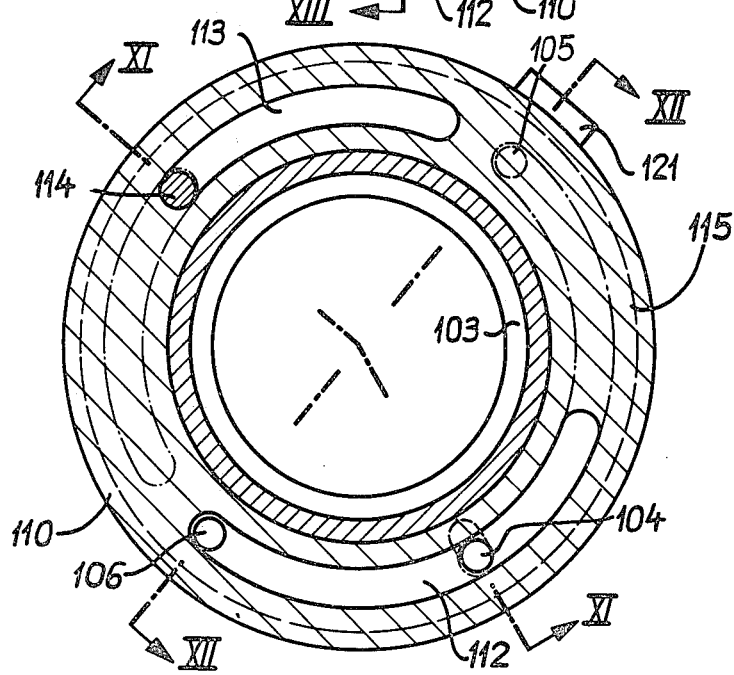

4,219,618

DENTAL HAND TOOL HOLDER

FIELD OF THE INVENTION

The present invention relates in general to tools used in dentistry and has specific reference to an improved dental handpiece.

More particularly, this invention refers to improvements in dental handpieces comprising essentially an elongated socket in which a central shaft is rotatably mounted for driving a tool adapted to be secured to the head of the handpiece, the rear end of the socket being adapted to be coupled or operatively connected to a driving member adapted in turn to rotate freely on the handpiece, an internal inlet aperture being provided in the coupling end of the socket to permit the supply of cooling fluid to the tool and communicating with an outlet passage directing said cooling fluid to the head of the handpiece.

DESCRIPTION OF THE PRIOR ART

It is known to use a dental handpiece of the type broadly set forth hereinabove which comprises suitable means for eliminating any handling step for connecting or disconnecting the cooling fluid conduits provided on the micro-motor and the handpiece, respectively, when coupling or uncoupling the latter. This means is disposed internally of the handpiece and also of the micro-motor in the coupling area thereof in order to afford a free relative rotary motion. With a handpiece of this type, it is contemplated as a rule to utilize a special driving member also provided in the coupling area with an internal passage for receiving the cooling fluid. Now, at present a great number of micromotors or driving members not provided with this internal passage are still available commercially and possessed by dentists and surgeon-dentists, and these expensive motors and driving members cannot be utilized with the new handpieces of the type mentioned hereinabove. It is therefore particularly advantageous to provide an improved dental handpiece capable of being coupled indifferently to both types of micro-motors with or without internal passage for the cooling fluid.

DESCRIPTION OF THE INVENTION

It is the essential object of the present invention to avoid the above-described inconveniences by providing an improved dental handpiece characterized in that it comprises an external inlet port or like aperture adapted to be connected to an external cooling-fluid supply hose, this port communicating with the outlet passage via a chamber into which said internal inlet aperture opens directly, a valve member mounted in said chamber and having two positions, namely a first position in which said internal inlet port is closed so that the circulation of cooling fluid between said external inlet port and said outlet passage can take place, and another position in which said external port is closed and the circulation of cooling fluid said internal inlet port and said outlet passage can take place.

BRIEF DESCRIPTION OF THE DRAWINGS

FIG. 11 is a sectional view of the rear end of a modified form of embodiment of the dental handpiece, the section being taken along the line XI—XI of FIG. 13;

FIG. 12 is a fragmentary sectional view taken along the line XII—XII of FIG. 13, and FIG. 13 is a cross section taken along the line XIII—XIII of FIG. 11.

DESCRIPTION OF THE PREFERRED EMBODIMENTS

Figure 1A:
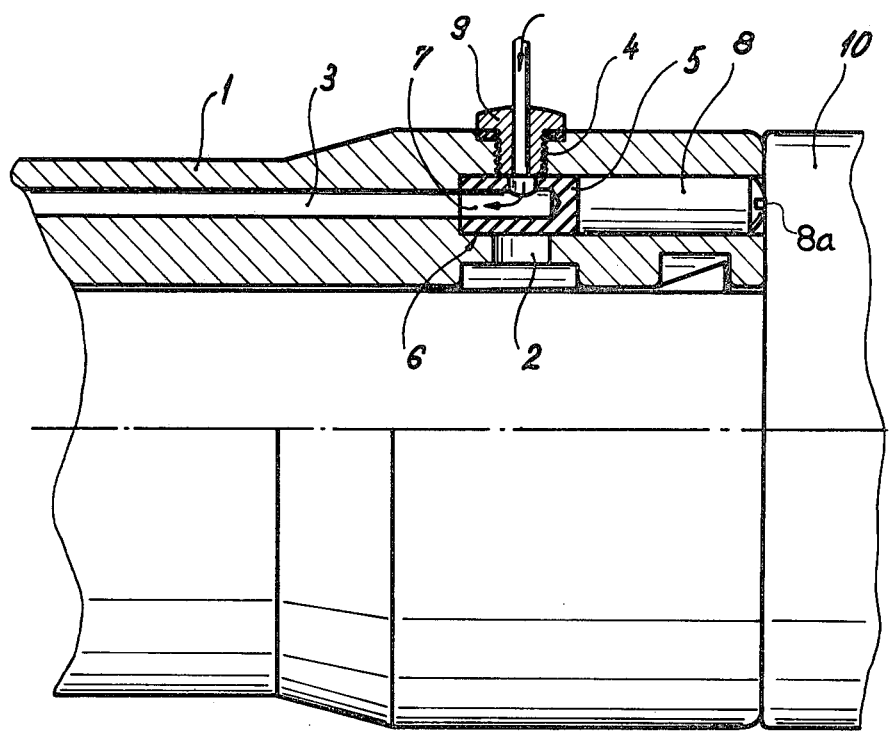
FIG. 1a is a part-elevational, part-sectional view showing the rear end of a dental handpiece in accordance with the invention adapted to be coupled to an obsolete micro-motor not provided with an internal passage for supplying cooling fluid to the dental tool, the micro-motor being shown only partially in the Figure.
Figure 1B:
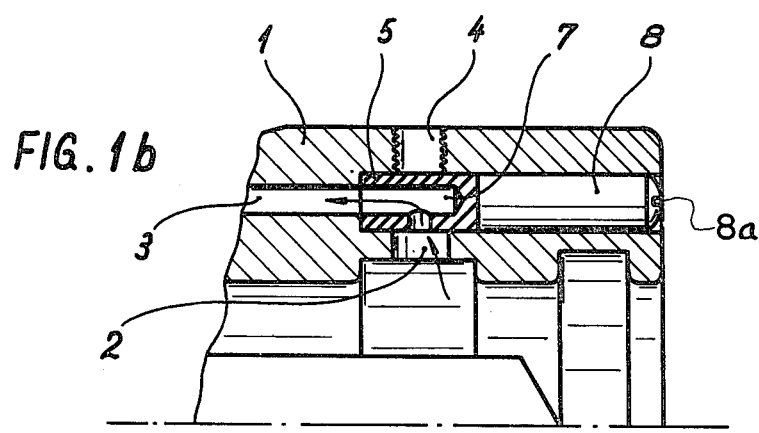
FIG. 1b is a view similar to FIG. 1a with the handpiece adapted to be coupled to another micro-motor (not shown) of the type provided with an internal passage for the cooling fluid.

Referring first to FIGS. 1a and 1b, the dental handpiece 1 has formed therein a radial inlet port 2 for supplying cooling fluid to the tool (not shown). This port 2 communicates with an outlet passage 3 directing the cooling fluid to the head of the handpiece. On the other hand, an external outlet port 4 in radial alignment with the internal inlet port 2 and also communicating with the outlet passage 3 is also provided. A valve member 5 is fitted in a chamber 6 disposed between ports 2 and 4 opening directly therewith like the outlet passage 3 in axial alignment with said chamber 6. This valve member 5 fills the chamber 6 completely and comprises an axial blind cavity 7 having radial or perpendicular extension at its inner end, as shown. This valve member is formed integrally with a blind or solid axial extension 8 of which the head is flush with the rear end face of the handpiece 1.

FIG. 1a shows only diagrammatically the coupling end of micro-motor 10 to which the handpiece 1 is secured in the known fashion by means of a spring-loaded device. In this example the micro-motor 10 does not comprise an internal passage for delivering cooling fluid to the tool. Besides, the outlet passage 3 of handpiece 1 may be either completely internal and formed longitudinally in the wall of the body of handpiece 1, or only partially internal in the rear coupling end thereof so that it can be connected to an external hose.

When the handpiece 1 is to be associated with a micro-motor 10 without any internal passage for supplying cooling fluid to the tool, as exemplified in FIG. 1a, valve member 5 is positioned to connect the external inlet port 4 via the internal passage 7 to the outlet passage 3 while closing the communication between the other or internal inlet port 2 and the outlet passage 3. Thus, the cooling fluid may circulate in the direction shown by the arrows. In this case, the inlet port 4 may consist of a tapped hole connected through a union 9 screwed therein to a flexible hose fitted into the central hole of this union, as shown.

When the handpiece 1 is to be associated with or coupled to a micro-motor 10 provided with an internal passage for supplying cooling fluid to the tool (FIG. 1b), the valve member 5 is rotated by means of a screw driver (not shown) through 180° in chamber 6, from its position shown in FIG. 1a, in order to set this valve member 5 in the position shown in FIG. 1b and connect the inner port 2 via the internal passage 7 of valve member 5 to the outlet passage 3 of handpiece 1 while closing the communication between the external inlet port 4 and the outlet passage 3. For this purpose, the rear end of rod 8 is provided with a diametral screwdriver slot 8a and also with a reference mark for displaying the setting of the internal passage 7 of valve member 5.

Figure 2A:
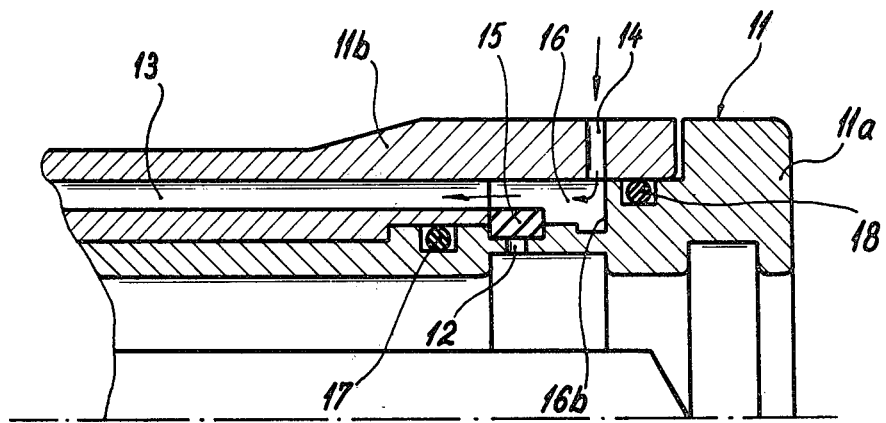
FIGS. 2a and 2b are fragmentary elevational and sectional views of a modified form of embodiment of the improved dental handpiece adapted to be coupled to a micro-motor with or without internal fluid passage, respectively.
Figure 2B:
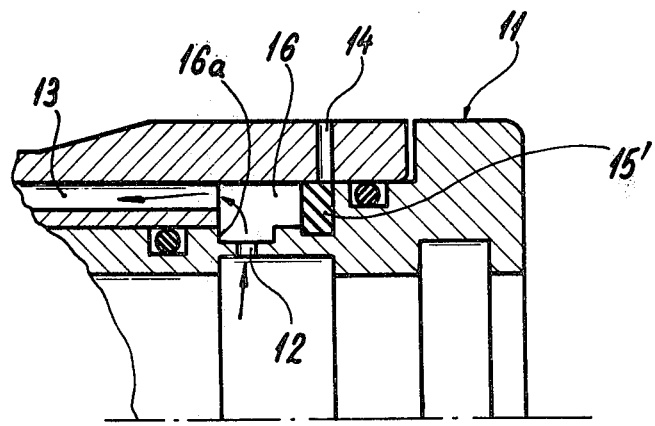

Referring now to FIGS. 2a and 2b, it will be seen that in this modified arrangement the dental handpiece 11, for the purpose of simplifying its manufacture and the machining of its component elements, consists of two sockets, namely an internal socket 11a screwed or snug fitted in an external socket 11b. An internal inlet port 12, an outlet passage 13 and an external inlet port 14 open into a chamber 16, respectively. The dimensions of this chamber 16 are such that two annular sealing members 15, 15' for example in the form of ring having a rectangular cross-section may be fitted alternatively in the device. More particularly, the first ring 15 (FIG. 2a) is adapted to fit snuggly in a first groove 16a formed in chamber 16 so that the fluid fed to the device through the external inlet port 14 can flow freely to the outlet passage 13 while closing the internal inlet port 12. The other ring 15' (FIG. 2b) is adapted on the other hand and alternatively to fit snuggly in another groove 16b so as to close the communication between the external inlet port 14 and the outlet passage 13 while permitting the flow of fluid from the internal inlet port 12 and said passage 13. O-rings 17, 18 are provided for sealing the mutually engaging surfaces of the outer socket 11a and internal socket 11b, as shown. If desired, the external inlet port 14 may also be connected to the supply hose (not shown) via a hollow union (not shown).

In this case, when it is desired to couple the handpiece 11 to a micro-motor provided or not with an internal passage for the cooling fluid, the inner socket 11a of the handpiece must be disassembled and one of the sealing rings 15, 15' must be positioned in the corresponding groove 16a or 16b; however, this conversion should preferably be carried out by the manufacturer.

In FIGS. 1a, 1b and 2a, 2b of the drawings, as well as in all the other Figures to which reference will be made subsequently in this specification, the arrows show the direction of flow of the cooling fluid.

Figure 3A:
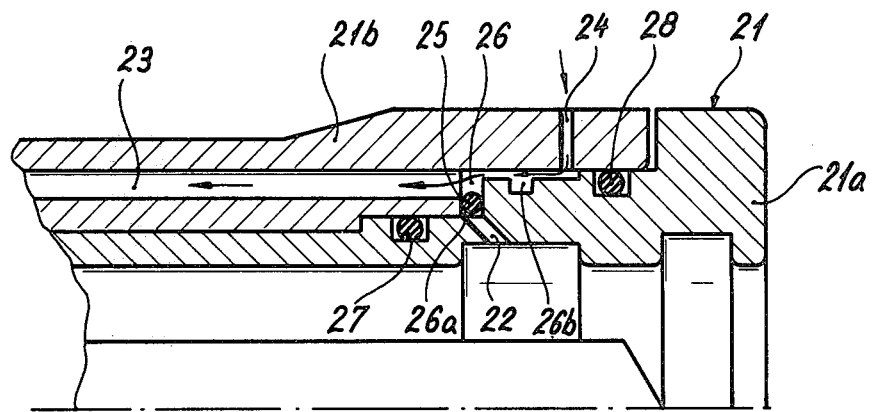
FIGS. 3a, 3b, to 8a, 8b illustrate also in fragmentary elevational and sectional views, respectively, third to eighth forms of embodiment of the improved dental handpiece of this invention.
Figure 3B:
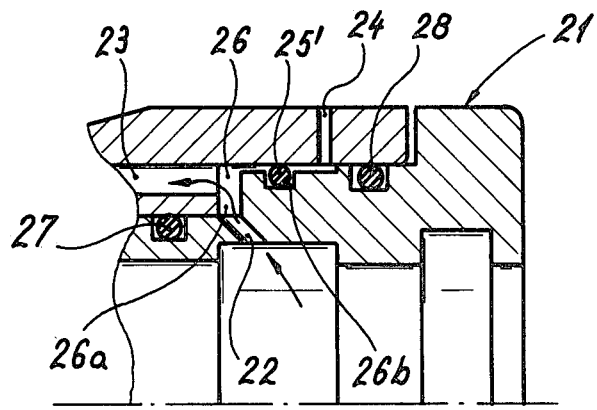

Referring now to FIGS. 3a and 3b of the drawings, the dental handpiece 21 illustrated therein comprises likewise a pair of sockets 21a, 21b assembled to each other for example by screw engagement. An oblique internal inlet port 22 inclined forwardly and outwardly in a radial plane, an outlet passage 23 and an external inlet port 24 open into a chamber 26. A pair of seals 25, 25' consisting each of an O-ring may be fitted manually and alternatively, the one 25 into a first circular cavity 26a (FIG. 3a), in order to close the communication between the internal inlet port 22 and the outlet passage 23, for adapting the handpiece to a micro-motor without internal passage, and the other 25' into another circular cavity 26b (FIG. 3b) for closing the communication between the external inlet port 24 and the outlet passage 23, for adapting the handpiece 21 to a micro-motor provided with an internal passage for the cooling fluid. In this specific form of embodiment, other O-rings 27, 28 are also provided for sealing the joint between the two sockets. The handpiece is thus easily adaptable to one or the other type of micro-motor by disassembling the sockets 21a and 21b.

Figure 4A:
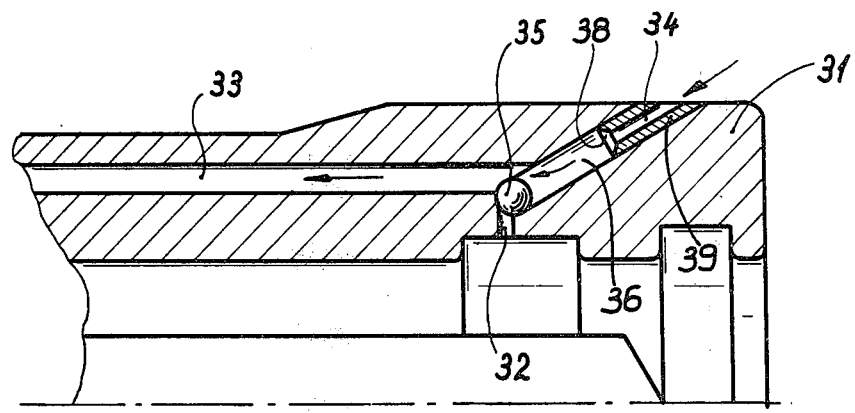
Figure 4B:
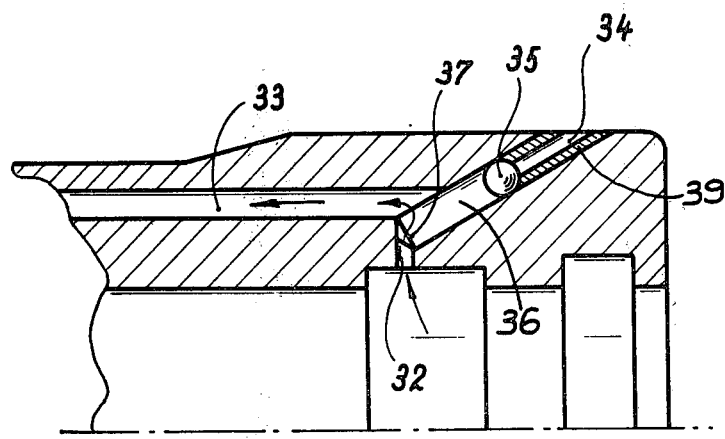

FIGS. 4a and 4b illustrate another form of embodiment wherein the dental handpiece 31 can be adapted automatically to either micro-motor types. In this case, the valve member consists of a ball 35 enclosed in a chamber 36 directed forwardly and inwardly in a radial plane and adapted to move from one valve seat 37 to another valve seat 38, and vice versa. A first valve seat 38 is formed at the end of an external inlet port 34 forming the outward extension of the oblique chamber 36, this valve seat being formed at the inner end of a tubular insert 39 force fitted into the outer end portion of the external inlet port 34. Another valve seat 37 is formed at the outer end of a radial internal inlet port 32 opening at its opposite end into said oblique chamber 36. The outlet passage 33 also opens into this oblique chamber 36 between the two ports 32 and 34.

When the handpiece 31 is coupled to a micro-motor without an internal passage for the cooling fluid (FIG. 4a), this fluid is fed thereto through the external inlet port 34 and its pressure causes the ball valve 35 to engage valve seat 37 in order to close the communication between the internal inlet port 32 and the outlet passage 33.

When the handpiece 31 is coupled to a micro-motor provided with an internal passage (FIG. 4b), the cooling fluid will be directed through the internal inlet port 32 and its pressure will force the ball valve 35 against the other seat 38 so as to close the communication between the external inlet port 34 and the outlet passage 33.

Figure 5A:
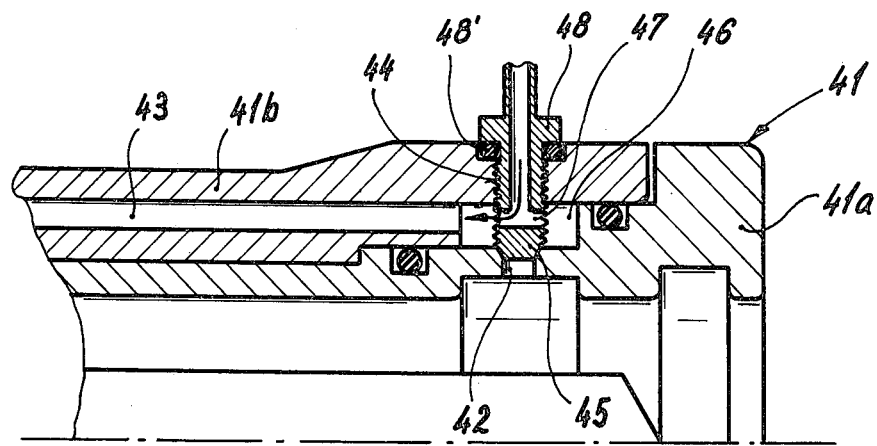
Figure 5B:
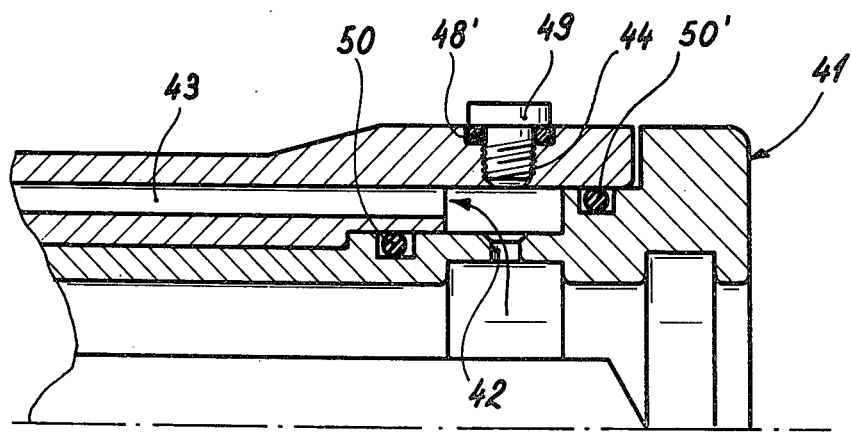

FIGS. 5a and 5b illustrate a fifth form of embodiment of the dental handpiece 41 comprising the outlet passage 43, the chamber 46 and the internal and external inlet ports 42 and 44 which, in this case, are aligned radially to each other. The external inlet port 44 is tapped and the internal inlet port 42 constitutes a valve seat at its end adjacent chamber 46. When the handpiece is to be associated with a micro-motor of the former or obsolete type, i.e. without any internal fluid passage, a union 48 is screwed into the tapped port 44; this union 48 is adapted to be connected to the supply hose and provided with a longitudinal axial passage opening into a diametral orifice 47 formed across this union and opening in turn into chamber 46 communicating with the outlet passage 43. The end 45 of union 48 is closed and its length is such that when this union 48 is screwed home in port 44, its inner end 45 acts as a plug by engaging the valve seat formed in the internal inlet port 42 so as to close the communication between this inlet port 42 and the outlet passage 43.

When the handpiece 41 is to be used with a micro-motor provided with an internal passage for the cooling fluid, a simple screw plug 49 is fitted in port 44 in lieu of union 48 and the communication is thus established between the internal inlet port 42 and the outlet passage 43. O-ring seals 48', 50 and 50' are provided for ensuring the necessary fluid-tightness of union 48 or plug 49, and between the mutually engaging surfaces of the pair of sockets 41a, 41b constituting the body of the handpiece.

Figure 6A:
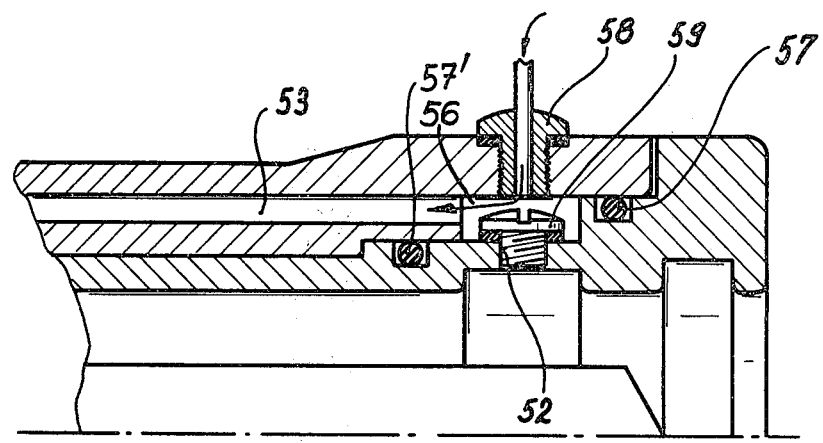
Figure 6B:
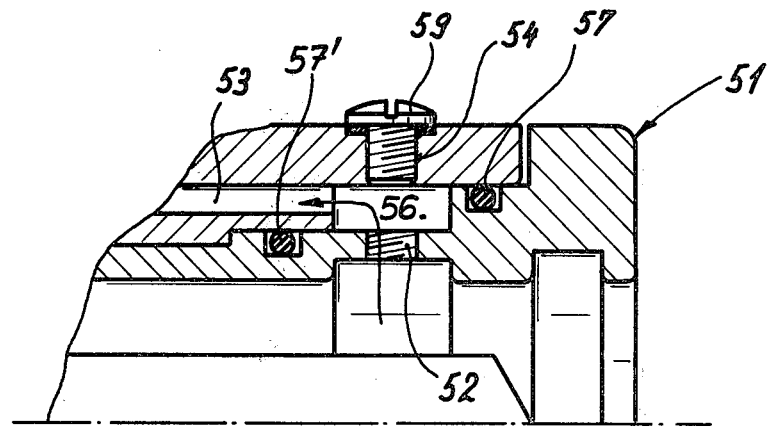

FIGS. 6a and 6b illustrate a form of embodiment almost similar to the preceding one, with the only difference that the internal inlet port 52 opening into chamber 56 is tapped and has the same diameter as the tapped external inlet port 54, so that the same plug 59 may be used for closing this external inlet port 54 (FIG. 6b) and permit the communication between the internal inlet port 52 and the outlet passage 53, i.e. for closing the internal inlet port 52 (FIG. 6a) and closing said communication. In this case, a union 58 is also provided for connecting the external inlet port 54 to the external supply hose (not shown). O-rings 57, 57' are also disposed between the two sockets constituting the body of the handpiece.

Figure 7A:
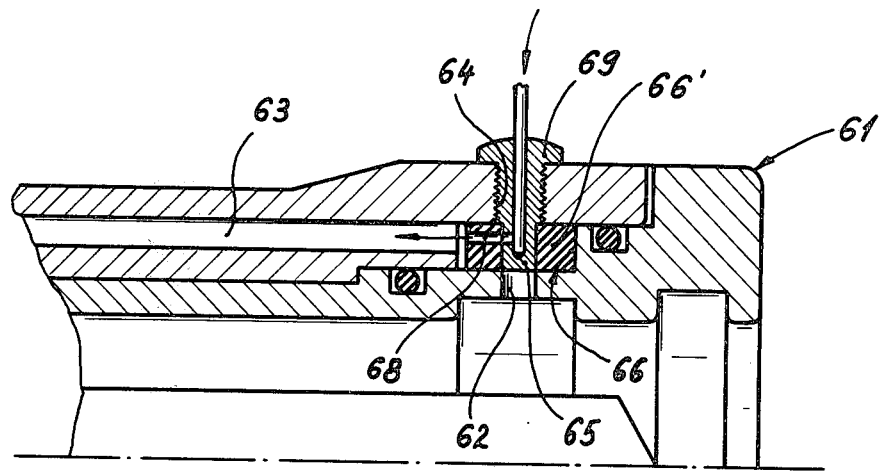
Figure 7B:
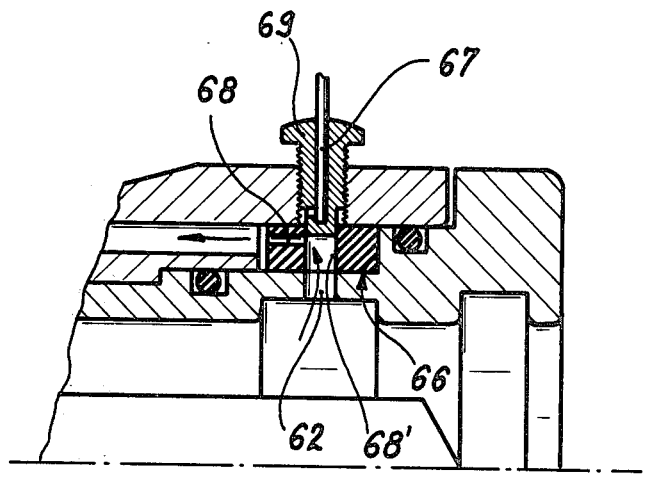

In the modified form of embodiment illustrated in FIGS. 7a and 7b, the internal inlet port 62 is also aligned radially with the external inlet port 64. Both ports 62 and 64 open into a chamber 66 from which an outlet passage 63 extends to the front or head of the handpiece. A seal 66' consisting of a block of suitable elastomeric material having the same radial section as chamber 66 is enclosed in this chamber and has a radial hole 68' formed therethrough in alignment with ports 62 and 64, another hole 68 formed at right angles to hole 68' and to the longitudinal axis of the elastomer seal 68' connecting this radial hole 68' to the outlet passage 63. A plug 69 acting as a union between the device and an external supply hose is screwed in the external inlet port 64 and has a central blind orifice 67 formed therein, and a radial hole is also formed in this plug and opens into the central orifice 67, as shown. The solid inner end 65 of plug 69 constitutes the valve member proper. The shape and dimensions of this plug 69 are such that when the latter is screwed home in the external inlet port 64 (FIG. 7a) and it is desired to operate the handpiece with a micro-motor without any internal passage, the radial orifice of plug 67 is aligned with the longitudinal hole 68 of seal 66', this permitting the communication between the external inlet port 64 and the outlet passage 63, while the valve-forming solid end portion 65 of said plug 67 closes the radial orifice 68' of seal 66' to prevent any fluid communication between the internal inlet port 62 and the outlet passage 63.

When the device is to be operated with a micro-motor provided with an internal fluid passage, it is only necessary to unscrew the plug 69 until its valve-forming solid end portion 65 uncovers the longitudinal orifice 68, so that the latter will permit the communication between the internal inlet port 62 and the outlet passage 63. This plug 69 should be screwed out only to the extent necessary and sufficient for uncovering the inner end of orifice 68 so that the solid inner end 65 of plug 69 will still close the upper end of radial hole 68' and thus prevent the communication between the external inlet port 64 and the outlet passage 63. With this arrangement, the same plug may advantageously be used for manually switching the handpiece from one type of micro-motor to another. Furthermore, with this modified form of embodiment it is also advantageous to provide a reference mark on the plug for displaying the position of the radial portion of orifice 67.

Figure 8A:
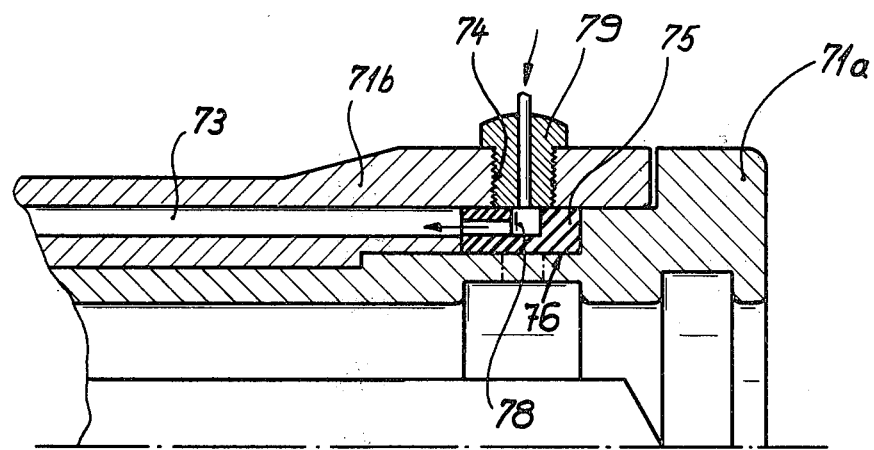
Figure 8B:
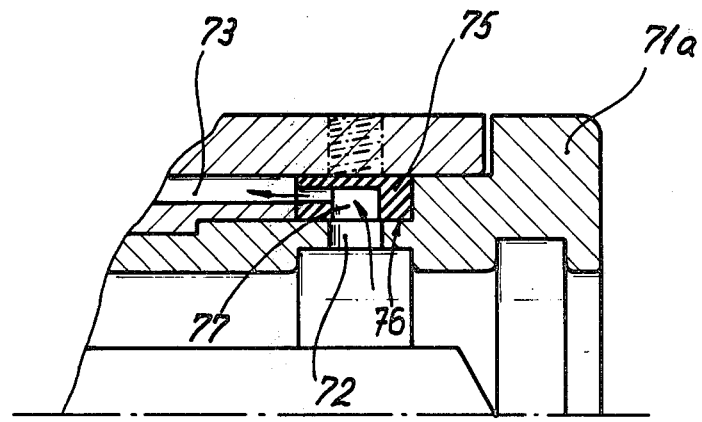

In the exemplary form of embodiment illustrated in FIGS. 8a and 8b, the seal 75 of elastomeric material has the shape of a circular segment and is fitted on the outer periphery of the internal socket 71a so as to fill completely the chamber 76 formed between said internal socket 71a and the external socket 71b; the axes of the external and internal inlet ports 74, 72 opening into this chamber 76 lie on a common transverse plane but are shifted angularly from each other. The seal 75 is provided with a pair of elbow-forming orifices 77, 78 having opposite directions, shifted angularly and so disposed as to cause the outlet passage 73 to communicate either with the external inlet port 74 (FIG. 8a) in case the handpiece is to be operated from and coupled to, a micro-motor without internal fluid passages, or with the internal inlet port 72 (FIG. 8b) when the device is to be coupled to a micro-motor having an internal fluid passage. Switching the outlet passage 73 to one or the other inlet ports 74, 72 is obtained by rotating the inner socket 71a in relation to the outer socket 71b. A reference mark is provided on the outer surface of these sockets for conveniently displaying the position of the elbow-forming orifices 77, 78. As in the preceding forms of embodiment, a union 79 may be screwed in the external inlet port 74.

Figure 9A:
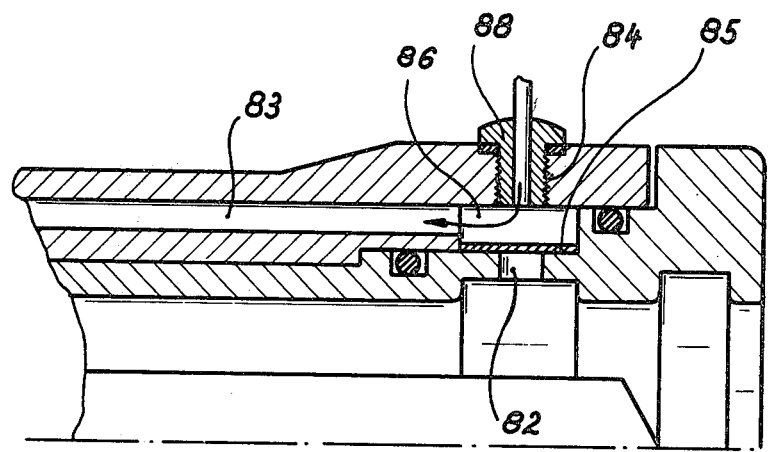
FIG. 9a is an elevational and sectional view of a ninth form of embodiment of the dental handpiece intended for coupling with a micro-motor provided with an internal passage.
Figure 9B:
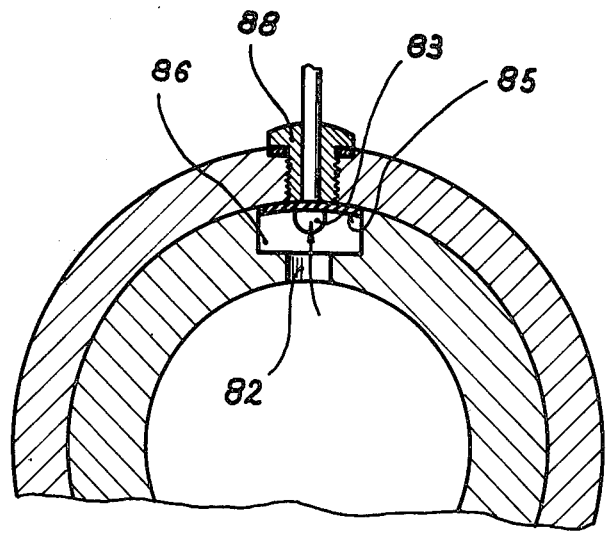
FIG. 9b is a cross-sectional view of the same handpiece as in FIG. 9a but adapted for coupling to a micromotor provided with an internal passage.

In the modified form of embodiment illustrated in FIGS. 9a and 9b, the internal inlet port 82 is also radially aligned with the external inlet port 84, both ports opening into a chamber 86 from which the outlet passage 83 extends towards the head of the handpiece. The valve member consists in this example of a small diaphragm 85 fitted in chamber 86 and movable to one or the other of two positions as a function of the mode of supplying cooling fluid to said head. When the handpiece is driven from a micro-motor without internal fluid passage (FIG. 9a), the cooling fluid flowing in the direction of the arrow through the external inlet port 84 possibly provided with a union 88 urges the diaphragm 85 to the bottom of chamber 86, thus closing the communication between the internal inlet port 82 and the outlet passage 83, so that the fluid can flow through the external inlet port 84 to said outlet passage 83.

Conversely, when the hand tool holder is operated from a micro-motor provided with an internal passage (FIG. 9b), the diaphragm 85 is urged by the fluid pressure against the top or outer wall of chamber 86 to close the communication between the external inlet port 84 and the outlet passage 83 while permitting the flow of fluid from the internal inlet port 82 to said outlet passage 83.

Figure 10A:
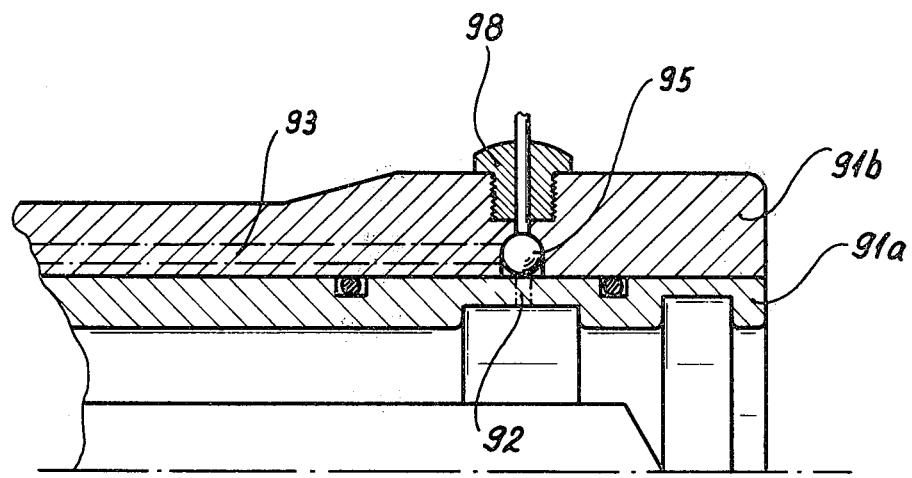
FIG. 10a is a part-elevational, part-sectional view of a tenth form of embodiment of the dental handpiece adapted to be coupled to a micro-motor without internal passage.
Figure 10B:
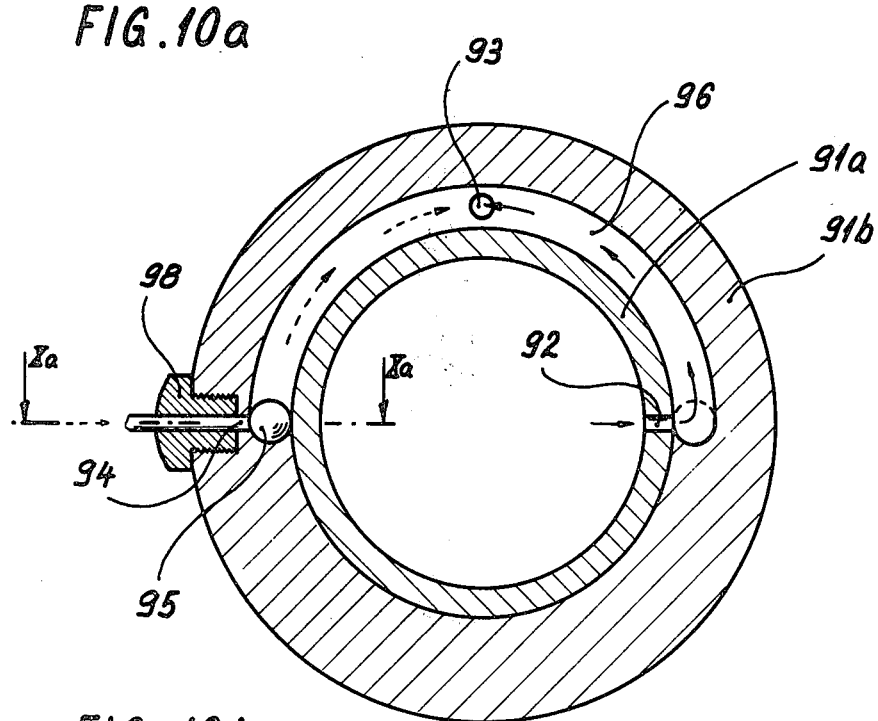
FIG. 10b is a cross sectional view of the handpiece shown in FIG. 10a but adapted to be connected to a micro-motor provided with an internal passage.

FIGS. 10a and 10b show a tenth form of embodiment of the dental handpiece according to this invention, wherein the internal and external inlet ports 92 and 94, respectively, are located in a same radial plane but shifted angularly from each other by the angular extent of a common chamber 93 consisting of a segment-shaped groove formed in the surface of the external socket 91b that contacts the internal socket 91a. The inlet ports 92, 94 are located at and open into the opposite ends of chamber 96, and the outlet passage 93 is equally spaced from said ports. In the example illustrated, the inlet ports are separated from each other by an angle of 180°, but of course other angles of shift may be contemplated without departing from the basic principle of the invention.

In this embodiment, the valve member consists of a ball 95 of rubber of other suitable plastic material; the diameter of this ball 95 is somewhat greater than that of the inlet ports opening into said chamber 96, and the ball valve can move from one end to the other end of chamber 96 for closing one or the other of the pair of ports 92, 94. The movement of ball valve 95 due to the fluid pressure depends on which inlet port is connected to the fluid feed line.

FIG. 10b illustrates in thick lines the ball 95 in the position obtained when the handpiece is coupled to a micro-motor having an internal passage and in dash lines the position of said ball 95 when the handpiece is coupled to a micro-motor without internal passage. The switching of the handpiece from one to the other type of micro-motor is therefore automatic as in the preceding example.

Reference will now be made to FIGS. 11 to 13 of the drawings which illustrate an eleventh form of embodiment of the invention which simplifies considerably the switching of the handpiece from one to the other type of micro-motor to be utilized, this switching being obtained by simply rotating a ring member, i.e. without compelling the user to disassemble a socket or resorting to a suitable or special tool.

The dental handpiece 101, of which only the rear end adapted to be coupled to the driving micro-motor is illustrated, comprises an external socket 102 having an internal socket 103 screwed therein. This external socket 103 comprises: a longitudinal outlet passage 104 adapted to convey the cooling fluid to the head of the device; an external inlet port 105 adapted to supply cooling fluid to the handpiece from a suitable external source such as an external hose; and an internal inlet port 106 for supplying cooling fluid to the handpiece from an internal source such as the passage formed in the micro-motor coupled to the device. The internal inlet port 106 communicates with a circular groove 107 formed on the external surface of internal socket 103, a radial hole 108 permitting the communication between said circular groove 107 and a second circular groove 107a formed on the inner surface of the internal socket 103, a radial hole formed in the micro-motor (not shown) opening into said second circular groove which communicates on the other hand with the internal supply passage formed in said micro-motor. This internal inlet port 106 is inclined forwardly and inwardly from the inner surface of external socket 102 to the end surface thereof. The external inlet port 105 is L-shaped and its end opening into the outer surface of the external socket 102 is screw-threaded for engagement either by a union 121 connected to the external fluid supply hose when the hand tool holder is coupled to a micro-motor without internal fluid passage or by a plug when this port must be closed for coupling the handpiece to a motor provided with an internal fluid passage.

The outlet passage 104, external inlet port 105 and internal inlet port 106 open into the rear end surface 109 of the external socket 102, the outlet passage 104 being disposed asymmetrically between the internal and external inlet ports 106 and 105 located at diametrally opposite locations.

A rotary ring 110 is disposed at the end of said external socket 102 and retained between this external socket 102 and a shoulder 111 of the internal socket 103. The face of the rotary ring 110 which is adjacent the end surface 109 of the external socket 102 has two grooves 112, 113 formed therein. These grooves have the shape of circular arcs, and the length of the first groove 112 is such that it provides a fluid connection between the outlet passage 104 and either the external inlet port 105 or the internal inlet port 106; besides, the second groove 113 is adapted to co-act with a pin 114 force-fitted into a blind hole formed in and projecting from the end surface of the external socket 102 for limiting and guiding the angular movements of said rotary ring 110 in relation to the external socket 102. The relative arrangement and the lengths of grooves 112 and 113 are so selected that when pin 114 abuts a first end of groove 113, the other groove 112 permits the communication between the outlet passage 104 and, for example, the internal inlet port 106, as illustrated in FIG. 13, and that when said ring 110 is rotated until pin 114 abuts the opposite end of groove 113, the other groove 112 provides a free communication between the outlet passage 104 and the external inlet port 105, as illustrated in dash and dot lines in FIG. 13. The asymmetrical position of outlet passage 104 between the two inlet ports 105 and 106 permits an appreciable reduction of the angular excursion of rotary ring 110 with respect to the external socket 102.

Disposed between the end surface of external socket 102 and the rotary ring 110 is a plastic or rubber gasket or seal 115 in the form of an annular washer provided at the locations corresponding to the inlet ports 105 and 106 and to outlet passage 104 with adequate holes, this gasket 115 being retained in contact with the end surface of the external socket 102 by said pin 114 extending through a corresponding orifice 116; on the other hand, this gasket 115 is fitted in a chambered portion 117 of said rotary ring 110.

In addition, O-rings 118 are disposed between the internal socket 103 and the external socket 102. According to a preferred embodiment of this device, the rotary ring 110 on its face opposite the one in which the grooves 112 and 113 are formed, comprises another groove 119 in which another O-ring 120 is fitted.

For utilizing this handpiece coupled to a micro-motor provided with an internal feed passage for the cooling fluid, it is only necessary to turn the rotary ring 110 to the position shown in FIG. 13, so that the outlet passage 104 will communicate with the internal inlet port 106; for adapting the handpiece to a micro-motor without this internal passage, it is only necessary to move said rotary ring 110 angularly through the angle corresponding to the length of groove 113 so that the outlet passage 104 will communicate with the external inlet port 105.

Of course, reference marks may be provided on the external socket and on the rotary ring for displaying at any time which specific inlet port is connected to the outlet passage of the device.

It is thought that the impovements provided by the present invention and many of its attendant advantages will be understood from the foregoing description and it be apparent that various changes may be made in the form, construction and arrangement of the parts thereof described without departing from the spirit and scope of the invention or sacrificing all of its material advantages, the forms hereinbefore described being merely exemplary embodiments thereof.

What is claimed is:

1. A dental handpiece comprising an elongated body having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, and valve means in said chamber and movable between a first position in which said internal inlet portion is closed and said external inlet portion communicates with said outlet passage to supply cooling fluid to said head from an external supply tube, and a second position in which said external inlet portion is closed and said internal inlet port communicates with said outlet passage to supply cooling fluid to said head from said fluid supply conduit of a driving unit, said external inlet port being aligned radially with said internal inlet port and said outlet passage opening into said chamber between said ports in a direction at right angles to an axis interconnecting said ports, and said valve member being a cylindrical member completely filling said chamber and having an elbow-shaped internal passage, said valve member being rotatable through 180° from the outside for causing said outlet passage to communicate via said elbow-shaped passage with either said internal inlet port or said external inlet port.

2. A dental handpiece comprising an elongated body having a head adapted to receive a dental tool and a rear end adapted to be coupled to a driving unit, said body having a central bore for rotatably supporting a shaft connecting said tool with said driving unit, an outlet passage extending from the rear end face of said body to said head for conducting cooling fluid to said head, an internal fluid inlet port for connection with a fluid supply conduit in said driving inlet, and an external fluid inlet port for connection with an external fluid supply tube, said internal and external inlet ports opening to the rear end surface of said body, and said outlet passage being disposed between said two inlet portions, and means for interconnecting said outlet passage alternatively with said internal inlet port and said external inlet port, said interconnecting means consisting of a rotary ring disposed at the rear end of said body and having its face adjacent said rear end of said body provided with at least one groove having the shape of a circular arc and a length such that in a first angular position of said ring said outlet passage is connected only to said internal inlet port and that in a second angular position of said ring said outlet passage is connected only to said external inlet port, means being also provided for limiting and guiding the permissible angular excursion of said rotary ring.

3. A dental handpiece according to claim 2, wherein said means for limiting and guiding the permissible angular excursion of said rotary ring consist of a groove having the shape of a circular arc, formed on the surface of said ring which is adjacent to the rear end of said body and adapted to co-act with a pin projecting from the end surface of said body.

4. A dental handpiece according to claim 3, wherein said body comprises a pair of concentrically interfitting external and internal sockets, and wherein said outlet passage and said internal and external inlet ports open into the end surface of the external socket and said rotary ring is mounted between said end surface of said external socket and a shoulder formed on said internal socket.

5. A dental handpiece according to claim 3, wherein a seal in the form of an annular washer of suitable elastomeric material is interposed between the end surface of said external socket and said rotary ring, suitable orifices being formed in said annular washer for proper registration with the locations corresponding to the internal and external inlet ports, and also to said outlet passage, respectively, and permitting the movement of said projecting pin.

6. A dental handpiece according to claim 3, wherein said outlet passage is disposed asymmetrically between said internal and external inlet ports in order to reduce the angular movement of said rotary ring with respect to said socket to the minimum value required for enabling said outlet passage to communicate with either of said internal and external inlet ports.

7. A dental handpiece according to claim 4, wherein O-rings are provided between said internal socket and said external socket, and between said internal socket and said rotary ring.

8. A dental handpiece according to claim 6, wherein said internal and external inlet ports are disposed at diametrally opposite locations.

9. A dental handpiece comprising an elongated body having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, and valve means in said chamber and movable between a first position in which said internal inlet port is closed and said external inlet port communicates with said outlet passage to supply cooling fluid to said head from an external supply tube, and a second position in which said external inlet port is closed and said internal inlet port communicates with said outlet passage to supply cooling fluid to said head from said fluid supply conduit of a driving unit, said external inlet port being aligned radially with said internal inlet port and said outlet passage opening into said chamber between said ports in a direction at right angles to an axis interconnecting said ports, said internal and external inlet ports having like internal threads, and said valve members consisting of a threaded plug adapted to be screwed into one or the other of said external and internal ports.

10. A dental handpiece comprising an elongated body having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, and valve means in said chamber and movable between a first position in which said internal inlet port is closed and said external inlet port communicates with said outlet passage to supply cooling fluid to said head from an external supply tube, and a second position in which said external inlet port is closed and said internal inlet port communicates with said outlet passage to supply cooling fluid to said head from said fluid supply conduit of a driving unit, said external inlet port being aligned radially with said internal inlet port and said outlet passage opening into said chamber between said ports in a direction at right angles to an axis interconnecting said ports, said external inlet port being internally threaded and said valve member consisting of a plug screwed into said external inlet port and having therein a bent inner passage for interconnecting said external inlet port and said outlet passage, and a solid end adapted to constitute a closing valve member between said outlet passage and either of said inlet ports.

11. A dental handpiece comprising an elongated body having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, and valve means in said chamber and movable between a first position in which said internal inlet port is closed and said external inlet port communicates with said outlet passage to supply cooling fluid to said head from an external supply tube, and a second position in which said external port is closed and said internal inlet port communicates with said outlet passage to supply cooling fluid to said head from said fluid supply conduit of a driving unit, said external inlet port being aligned radially with said internal inlet port and said outlet passage opening into said chamber between said ports in a direction at right angles to an axis interconnecting said ports, said valve member consisting of a movable diaphragm disposed in said chamber and movable by the pressure of the cooling fluid against either of said inlet ports.

12. A dental handpiece comprising an elongated body consisting of two concentrically interfitting internal and external sockets and having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, said external inlet port being disposed in the same radial plane as said internal inlet port but shifted angularly in relation thereto, said outlet passage opening into said chamber between said two inlet ports, and valve means in said chamber and movable between a first position in which said internal inlet port is closed and said external inlet port communicates with said outlet passage to supply cooling fluid to said head from an external supply tube, and a second position in which said external inlet port is closed and said internal inlet port communicates with said outlet passage to supply cooling fluid to said head from said fluid supply conduit of a driving unit.

13. A dental handpiece according to claim 12, wherein said chamber consists of a segment-shaped groove formed in the surface of the external socket contacting said internal socket, said valve member consisting of a ball having a diameter greater than the diameter of said external and internal inlet ports, said ball valve being movable within said chamber for alternatively closing either of said ports under the pressure of the said cooling fluid.

14. A dental handpiece according to claim 12, wherein said chamber consists of a groove having the shape of an annular segment formed between said internal and external inlet ports, said valve member being secured to said internal socket, having likewise the shape of an annular segment and filling the volume of said chamber completely, said valve member having formed therein a pair of interconnected L-shaped orifices extending at right angles to each other so as to open into opposite inner and outer faces of said valve member but having a relative angular shift between them, whereby rotating said internal socket in said external socket will enable said outlet passage to communicate with either of said inlet ports via either of said L-shaped orifices.

15. A dental handpiece comprising an elongated body comprising two concentrically interfitting sockets and having a head adapted to receive a dental tool and a rear end adapted to be coupled to a driving unit, said body having a central bore for rotatably supporting a shaft connecting said tool with said driving unit, a chamber in a rear portion of said body, an outlet passage extending from said chamber, to the head of said body for conducting cooling fluid to said head, an internal fluid inlet port opening from said chamber to the rear end face of said body for connection with a fluid supply conduit in said driving unit and an external fluid inlet port opening from said chamber to the peripheral outer surface of a rear end portion of said body for connection with an external fluid supply tube, said external inlet port being shifted in the axial direction with respect to said internal inlet port, and valve means in said chamber and movable between a first position in which said internal inlet port is closed and said external inlet port communicates with said outlet passage to supply cooling fluid to said head from an external supply tube, and a second position in which said external inlet port is closed and said internal inlet port communicates with said outlet passage to supply cooling fluid to said head from said fluid supply conduit of a driving unit, said valve member being adapted to be located manually in suitable cavities of said chamber for closing the communication between said outlet passage and either of said inlet ports.

16. A dental handpiece according to claim 15, wherein a pair of rectangular-sectioned rings or a pair of O-rings acting by turns as valve members are fitted alternatively the one into one of said cavities and the other to the other of said cavities.

* * * * *